US00PP20606P2

(12) United States Plant Patent
Hofmann

(10) Patent No.: US PP20,606 P2
(45) Date of Patent: Dec. 22, 2009

(54) ***BEGONIA* PLANT NAMED 'INNBELLPEA'**

(50) Latin Name: *Begonia×tuberhybrida*
Varietal Denomination: Innbellpea

(75) Inventor: Silvia Hofmann, Mainz (DE)

(73) Assignee: InnovaPlant GmbH + Co. KG, Gensingen (DE)

( * ) Notice: Subject to any disclaimer, the term of this patent is extended or adjusted under 35 U.S.C. 154(b) by 0 days.

(21) Appl. No.: 12/286,068

(22) Filed: Sep. 26, 2008

(51) Int. Cl.
*A01H 5/00* (2006.01)

(52) U.S. Cl. ..... Plt./347

(58) Field of Classification Search ..... Plt./347

See application file for complete search history.

*Primary Examiner*—Kent L Bell
(74) *Attorney, Agent, or Firm*—C. A. Whealy

(57) ABSTRACT

A new and distinct cultivar of *Begonia* plant named 'Innbellpea', characterized by its compact and mounded plant habit; freely branching habit; dense and bushy growth habit; dark green-colored leaves; numerous double flowers that are light apricot in color; and tolerance to Powdery Mildew.

1 Drawing Sheet

Botanical designation: *Begonia×tuberhybrida.*
Cultivar denomination: 'Innbellpea'.

BACKGROUND OF THE INVENTION

The present invention relates to a new and distinct cultivar of *Begonia* plant, botanically known as *Begonia×tuberhybrida* and hereinafter referred to by the name 'Innbellpea'.

The new *Begonia* plant is a product of a planned breeding program conducted by the Inventor in Gensingen, Germany. The objective of the breeding program was to develop new compact *Tuberhybrida Begonia* cultivars with attractive double flowers.

The new *Begonia* plant originated from a cross-pollination made by the Inventor in January, 2005 of a proprietary selection of *Begonia×tuberhybrida* identified as code number B 04 3-56, not patented, as the female, or seed, parent with a proprietary selection of *Begonia×tuberhydrida* identified as code number B 04 3-91, not patented, as the male, or pollen, parent. The new *Begonia* was discovered and selected by the Inventor as a single plant from within the progeny of the stated cross-pollination in a controlled greenhouse environment in Gensingen, Germany in September, 2005.

Asexual reproduction of the new *Begonia* plant by vegetative cuttings in a controlled greenhouse environment in Gensingen, Germany since October, 2005, has shown that the unique features of this new *Begonia* plant are stable and reproduced true to type in successive generations.

SUMMARY OF THE INVENTION

Plants of the new *Begonia* have not been observed under all possible environmental conditions. The phenotype may vary somewhat with variations in environment such as temperature and light intensity, without, however, any variance in genotype.

The following traits have been repeatedly observed and are determined to be the unique characteristics of 'Innbellpea'. These characteristics in combination distinguish 'Innbellpea' as a new and distinct cultivar of *Begonia:*

1. Compact and mounded plant habit.
2. Freely branching habit; dense and bushy growth habit.

3. Dark green-colored leaves.
4. Numerous double flowers that are light apricot in color.
5. Tolerant to Powdery Mildew.

Plants of the new *Begonia* differ from plants of the female parent selection in the following characteristics:

1. Plants of the new *Begonia* are more compact than plants of the female parent selection.
2. Plants of the new *Begonia* are more freely branching than plants of the female parent selection.
3. Flowers of plants of the new *Begonia* are double whereas flowers of plants of the female parent selection are semi-double.
4. Plants of the new *Begonia* and the female parent selection differ in flower color as plants of the female parent selection have soft pink-colored flowers.

Plants of the new *Begonia* differ from plants of the male parent selection in the following characteristics:

1. Plants of the new *Begonia* are more upright than and not as trailing as plants of the male parent selection.
2. Flowers of plants of the new *Begonia* are double whereas flowers of plants of the male parent selection are semi-double.
3. Plants of the new *Begonia* and the male parent selection differ in flower color as plants of the male parent selection have soft pink-colored flowers.

Plants of the new *Begonia* can also be compared to plants of the *Begonia×tuberhybrida* 'Lorelei', not patented. In side-by-side comparisons conducted in Gensingen, Germany, plants of the new *Begonia* differed from plants of 'Lorelei' in the following characteristics:

1. Plants of the new *Begonia* were more vigorous than plants of 'Lorelei'.
2. Plants of the new *Begonia* were more freely branching than plants of 'Lorelei'.
3. Leaves of plants of the new *Begonia* were lighter green in color than leaves of plants of 'Lorelei'.
4. Plants of the new *Begonia* and 'Lorelei' differed in flower color as plants of 'Lorelei' had dark orange-colored flowers.

BRIEF DESCRIPTION OF THE PHOTOGRAPHS

The accompanying colored photographs illustrate the overall appearance of the new *Begonia*, showing the colors as true as it is reasonably possible to obtain in colored reproductions of this type. Colors in the photographs may differ slightly from the color values cited in the detailed botanical description which accurately describe the colors of the new *Begonia* plant.

The photograph at the bottom of the sheet comprises a side perspective view of a typical flowering plant of 'Innbellpea' grown in a container.

The photograph at the top of the sheet is a close-up view of typical flowers and leaves of 'Innbellpea'.

DETAILED BOTANICAL DESCRIPTIONS

Plants used for the aforementioned photographs and following observations and measurements were grown in Carleton, Mich. in one-gallon containers and under commercial practice under partial shade in an outdoor nursery during the late summer. During the production of the plants, day temperatures ranged from 26° C. to 29° C., night temperatures ranged from 13° C. to 21° C. and light levels ranged from 6,000 to 7,000 foot-candles. Plants used for the photographs and the description were twelve weeks from planting. In the following description, color references are made to The Royal Horticultural Society Colour Chart, 2001 Edition, except where general terms of ordinary dictionary significance are used.

Botanical classification: *Begonia×tuberhybrida* 'Innbellpea'.

Parentage:

*Female, or seed, parent*.—Proprietary selection of *Begonia×tuberhybrida* identified as code number B 04 3-56, not patented.

*Male, or pollen, parent*.—Proprietary selection of *Begonia×tuberhybrida* identified as code number B 04 3-91, not patented.

Propagation:

*Type*.—By vegetative cuttings.

*Time to initiate roots, summer*.—About 7 to 10 days at temperatures of about 18° C. to 24° C.

*Time to initiate roots, winter*.—About 9 to 14 days at temperatures of about 18° C. to 24° C.

*Time to produce a rooted young plant, summer*.—About four weeks at temperatures of about 18° C. to 24° C.

*Time to produce a rooted young plant, winter*.—About five weeks at temperatures of about 18° C. to 24° C.

*Root description*.—Fine, fibrous; white in color. Plants of the new *Begonia* have not been observed to form tubers.

*Rooting habit*.—Moderate branching; moderately dense.

Plant description:

*Plant and growth habit*.—Compact and mounded plant habit; freely branching with about six to seven branches per plant; dense and bushy growth habit; moderately vigorous growth habit.

*Plant height*.—About 16 cm.

*Plant width*.—About 18 cm by 20 cm.

*Branch description*: Length: About 14 cm. Diameter: About 5 mm. Internode length: About 2 cm. Texture: Sparsely pubescent. Color: Close to 148A.

*Leaf description*.—Arrangement: Alternate; simple. Length: About 12.8 cm. Width: About 4.5 cm. Shape: Narrowly elliptic to narrowly cordate; asymmetrical. Apex: Acute. Base: Asymmetrically cordate. Margin: Bi-serrate. Texture, upper and lower surfaces: Smooth, glabrous. Venation pattern: Palmate; reticulate. Color: Developing leaves, upper surface: Close to 146A. Developing leaves, lower surface: Close to 181A. Fully expanded leaves, upper surface: Close to 139A; venation, close to 147B. Fully expanded leaves, lower surface: Close to 147B tinted with close to 181A to 181B; venation, close to 147B to 147C. Petiole length: About 2 cm. Petiole diameter: About 3 mm. Petiole texture, upper and lower surfaces: Sparsely pubescent. Petiole color, upper surface: Close to 148A. Petiole color, lower surface: Close to 199C.

Flower description:

*Flowering habit*.—Rounded sterile double flowers; flowers axillary. Freely flowering habit with about seven to ten flowers and flower buds per lateral branch. Flowers outwardly drooping.

*Fragrance*.—None detected.

*Natural flowering season*.—Plants flower continuously during the spring and summer in Germany. Flowers last about three to five days on the plant; flowers not persistent.

*Flower buds*.—Shape: Oval. Length: About 2 cm. Diameter: About 1.1 cm. Color: Close to 35B.

*Flowers*.—Diameter: About 5.4 cm. Depth (height): About 3.6 cm.

*Tepals*.—Arrangement: Rosette. Quantity per flower: About 98 per flower arranged in ten to twelve whorls. Length, largest tepals: About 3.5 cm. Width, largest tepals: About 8 mm. Shape: Ligulate. Apex: Acute. Base: Attenuate. Margin: Entire. Texture, upper and lower surfaces: Smooth, glabrous; velvety. Color: When opening, upper surface: Close to 37B. When opening, lower surface: Close to 39B. Fully opened, upper surface: Close to 38B to 38C; color becoming closer to 38C to 38D with development. Fully opened, lower surface: Close to 37A to 37C; color becoming closer to 37B to 37D with development.

*Flower bracts*.—Quantity/arrangement: Two, opposite. Length: About 2.5 cm. Diameter: About 2 cm. Shape: Elliptic. Apex: Acute. Base: Rounded. Margin: Entire. Texture, upper and lower surfaces: Smooth, glabrous. Color, upper surface: Close to 29B to 29C. Color, lower surface: Close to 30A to 30B.

*Peduncles*.—Angle: About 45° from the stem axis. Length: About 1.8 cm. Diameter: About 1.5 mm. Texture: Smooth, glabrous. Color: Close to 145C.

*Reproductive organs*.—Stamens: None observed. Pistils: None observed.

*Seed/fruit*.—Seed and fruit production have not been observed.

Disease/pest resistance/tolerance: Plants of the new *Begonia* have been observed to have good tolerance to Powdery Mildew. Resistance/tolerance to pests and other pathogens common to *Begonia* has not been observed.

Temperature tolerance: Plants of the new *Begonia* have been observed to tolerate temperatures from about 5° C. to about 35° C.

It is claimed:

1. A new and distinct *Begonia* plant named 'Innbellpea' as illustrated and described.

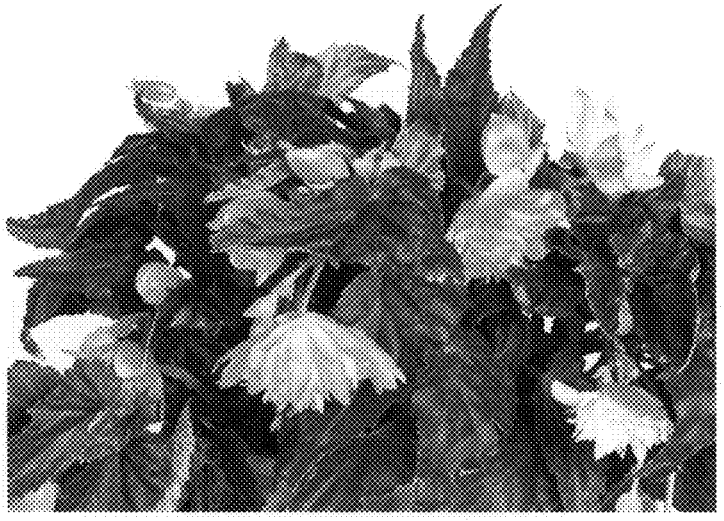
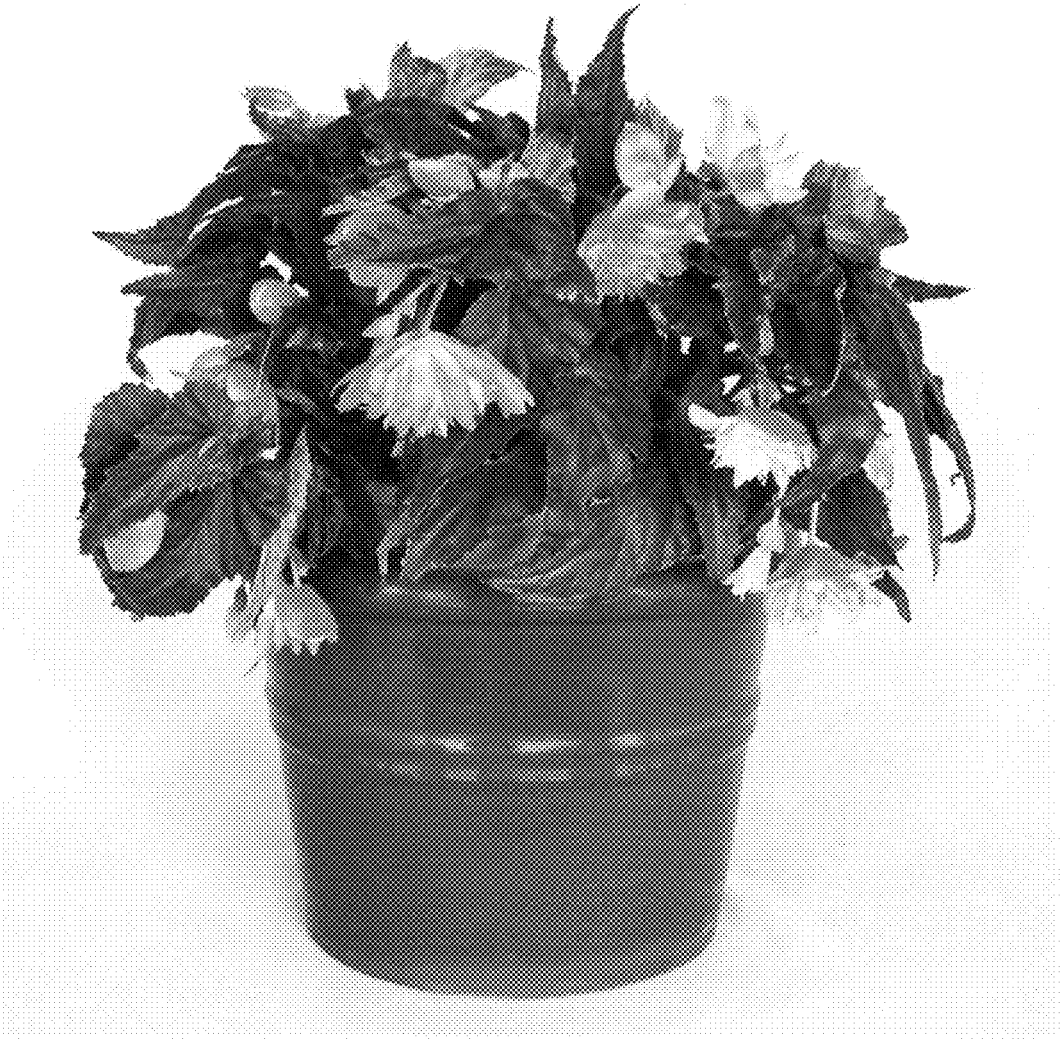

* * * * *